United States Patent
Ashdown (10) Patent No.: US 11,590,252 B2
(45) Date of Patent: Feb. 28, 2023

(54) PREDICTING SPHERICAL IRRADIANCE FOR VOLUME DISINFECTION

(71) Applicant: SUNTRACKER TECHNOLOGIES LTD., Victoria (CA)

(72) Inventor: Ian Edward Ashdown, West Vancouver (CA)

(*) Notice: Subject to any disclaimer, the term of this patent is extended or adjusted under 35 U.S.C. 154(b) by 0 days.

(21) Appl. No.: 17/632,442

(22) PCT Filed: Jul. 8, 2021

(86) PCT No.: PCT/CA2021/050935
§ 371 (c)(1),
(2) Date: Feb. 2, 2022

(87) PCT Pub. No.: WO2022/006675
PCT Pub. Date: Jan. 13, 2022

(65) Prior Publication Data
US 2022/0288261 A1    Sep. 15, 2022

Related U.S. Application Data (60) Provisional application No. 63/208,798, filed on Jun. 9, 2021, provisional application No. 63/116,371, filed (Continued)

(51) Int. Cl.
*A61L 2/24* (2006.01)
*G06F 30/10* (2020.01)
(Continued)

(52) U.S. Cl.
CPC .................. *A61L 2/24* (2013.01); *A61L 2/10* (2013.01); *A61L 2/28* (2013.01); *A61L 9/18* (2013.01);
(Continued)

(58) Field of Classification Search
CPC ..... A61L 2/10; A61L 2/28; A61L 2/24; A61L 9/18; A61L 2202/11; A61L 2202/14
See application file for complete search history.

(56) References Cited

U.S. PATENT DOCUMENTS 9,625,583 B2    4/2017 Beddar
2003/0147770 A1    8/2003 Brown
(Continued)

FOREIGN PATENT DOCUMENTS

CA    2796159    12/2011
WO    2018130403    7/2018
(Continued)

OTHER PUBLICATIONS

CIE System for Metrology of Optical Radiation for ipRGC-Influenced Responses to Light, CIE S 026/E:2018.
(Continued)

*Primary Examiner* — Sean E Conley (57) ABSTRACT

Given the complexity of architectural spaces and the need to calculate spherical irradiances, it is difficult to determine how much ultraviolet radiation is necessary to adequately kill airborne pathogens. An interior environment with luminaires is modeled. Spherical irradiance meters are positioned in the model and the direct and indirect spherical irradiance is calculated for each sensor. From this, an irradiance field is interpolated for a volume of interest, and using known fluence response values for killing pathogens, a reduction in the pathogens is predicted. Based on the predicted reduction, spaces are built accordingly, and ultraviolet luminaires are installed and controlled.

20 Claims, 7 Drawing Sheets

Related U.S. Application Data on Nov. 20, 2020, provisional application No. 63/105,149, filed on Oct. 23, 2020, provisional application No. 63/049,292, filed on Jul. 8, 2020.

(51) Int. Cl.
  *A61L 2/10* (2006.01)
  *A61L 2/28* (2006.01)
  *A61L 9/18* (2006.01)
  *C02F 1/32* (2006.01)
  *G01J 1/42* (2006.01)

(52) U.S. Cl.
  CPC ............ *C02F 1/32* (2013.01); *G01J 1/429* (2013.01); *G06F 30/10* (2020.01); *A61L 2202/11* (2013.01); *A61L 2202/14* (2013.01); *A61L 2202/25* (2013.01); *A61L 2209/111* (2013.01); *A61L 2209/12* (2013.01); *A61L 2209/16* (2013.01); *C02F 2209/001* (2013.01); *C02F 2303/04* (2013.01); *G01J 2001/4247* (2013.01)

(56) References Cited

U.S. PATENT DOCUMENTS

2017/0086274 A1  3/2017  Soler
2019/0209585 A1  7/2019  Slaughter

FOREIGN PATENT DOCUMENTS

WO  2018227305  12/2018
WO  2020221840  11/2020

OTHER PUBLICATIONS

Bellia, L., and F. Bisegna. 2013. "From Radiometry to Circadian Photometry: A Theoretical Approach," Building and Environment 62:63-68.
The Well Building Standard v1 with Q1 2019 Addenda.
UL RP 24480, Recommended Practice and Design Guideline for Promoting Circadian Entrainment with Light for Day-Active People.
Ashdown, I. 2019. "Challenging the Circadian Metric," LD+A December, pp. 36-39.
Lee, R. Lr, and J. Hernández-Andrés. 2006. "Colors of the Daytime Overcast Sky," Applied Optics 44(27):5712-5722.
Ashdown, I. 2019. "Climate-based Annual Daylight Modelling for Greenhouses with Supplemental Electric Lighting," ISHS Acta Horticulturae 1296, International Symposium in Advanced Technologies and Management for Innovative Greenhouses: GreenSys 2019, pp. 583-590.
Ashdown, I. 2017. "Analytic BSDF Modeling for Daylight Design," IES Annual Conference, Portland, OR, Aug. 10-12.
Luckiesh, M., and S. K. Guth. 1949. "Brightnesses in Visual Field at Borderline Between Comfort and Discomfort (BCD)," Illuminating Engineering, November, pp. 650-670.
Turner, P. L., and M. A. Mainster. 2008. "Circadian Photoreception: Ageing and the Eye's Important Role in Systemic Health," British Journal of Ophthalmology 92:1439-1444.
Barroso, A., et al. 2014. "Metrics of Circadian Lighting for Clinical Investigations," Lighting Research and Technology 46:637-649.
Hong et al. 2018. "Occupant Behavior Models: A Critical Review of Implementation and Representation Approaches in Building Performance Simulation Programs," Building Simulation 11(1):1-14.
Phillips, A. J. K., et al. 2019. "High Sensitivity and Interindividual Variability in the Response of the Human Circadian System to Evening Light," PNAS (https://doi.org/10.1073/pnas.1901824116).
Walmsley, L., et al. 2015. "Colour as a Signal for Entraining the Mammalian Circadian Clock," PLOS Biology 13(4):e1002127.
Hubbard, K., and A. Dodd. 2016. "Rhythms of Life: The Plant Circadian Clock," The Plant Cell, April, pp. 1-10.
Pauers, M. J., et al. et al. 2012. "Changes in the Colour of Light Cue Circadian Activity," Animal Behavior 83(5):1143-1151.
Ashdown, I. 1994. Radiosity: A Programmer's Perspective. New York, NY: John Wiley & Sons.
Guth, S. K. 1951. "Brightness Relationships for Comfortable Seeing," Journal of the Optical Society of America 41(4):235-244.
Levin, R. E. 1975. "Position Index in VCP Calculations," Journal of the Illuminating Engineering Society 4(2):99-105.
Jakubiec. J. A. and C. F. Reinhart. 201. "The 'Adaptive Zone' —A Concept for Assessing Discomfort Glare throughout Daylight Space," Lighting Research and Technology 44(2)149-170.
Bruneton, E. 2016. "A Qualitative and Quantitative Evaluation of 8 Clear Sky Models," IEEE Transactions on Visualization and Computer Graphics 23(12):2641-2655.
Patterson, S. S., et al. 2020. "A Color Vision Circuit for Non-Image-Forming Vision in the Primate Retina," Current Biology 30:1.

IRRADIANCE          FLUENCE RATE

PREDICTING SPHERICAL IRRADIANCE FOR VOLUME DISINFECTION

TECHNICAL FIELD

The subject matter of the present invention relates to the prediction of spherical irradiance in geometrically complex environments. In particular, it relates to the prediction of UV spherical irradiance for disinfecting interior environments.

BACKGROUND

Ultraviolet radiation has been used to disinfect the air in hospitals and other healthcare facilities for over eighty years. Aerosols that are generated by infected patients coughing, sneezing, or even talking may contain bacteria or viruses responsible for such diseases as tuberculosis, measles, chickenpox, smallpox, SARS, MERS, Ebola, and COVID-19.

Figure 1:
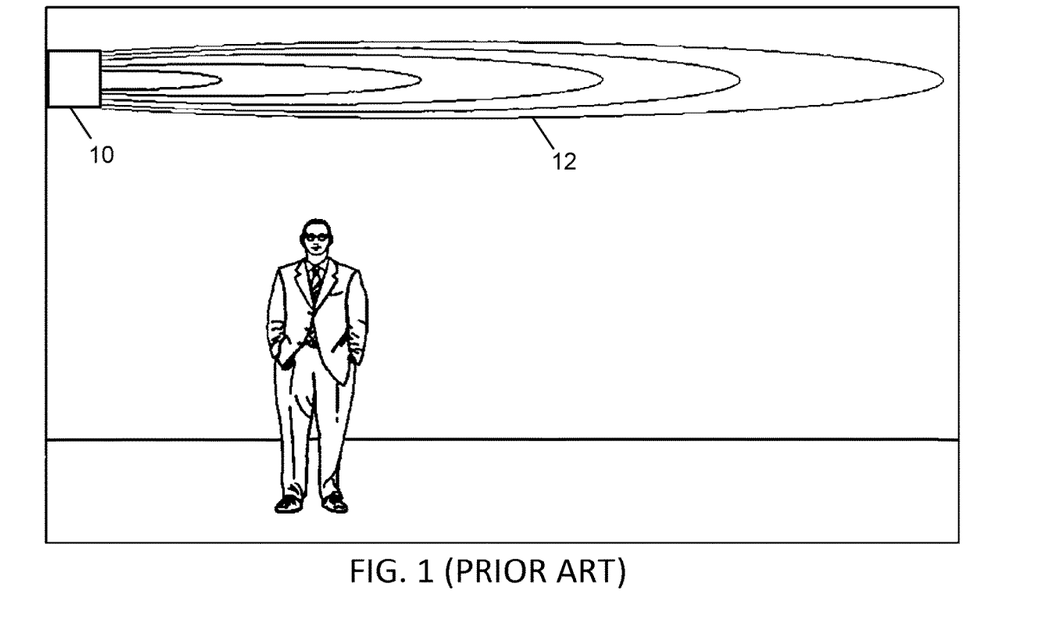
FIG. 1, prior art, shows an empty rectangular room divided into an upper room with a UVGI luminaire and an occupied lower room.

In a typical application in FIG. 1 (adapted from Kowalski 2009), ultraviolet-emitting lamps 10 with appropriate shielding are mounted on the wall above the line of sight of the room occupants (usually referred to as the "upper room") and their radiation 12 directed horizontally to irradiate the aerosol particles. The irradiation zone is above a height of 2.1-2.5 m (7-8 feet) and the amount of irradiation is 0.005-0.01 W/m$^2$. The lower room irradiance levels are <0.002 W/m$^2$ for UV-C and <0.001 W/m$^2$ for broadband UV. The ultraviolet radiation is absorbed by proteins, DNA, and RNA within the pathogen cells, which in turn damages their nucleic acids, causing cell death in bacteria and inactivation in viruses. Critically, the disinfected air must be regularly exchanged with outside air and circulated throughout the lower occupied room space using ceiling fans or forced-air ventilation to benefit the room occupants.

Figure 2:
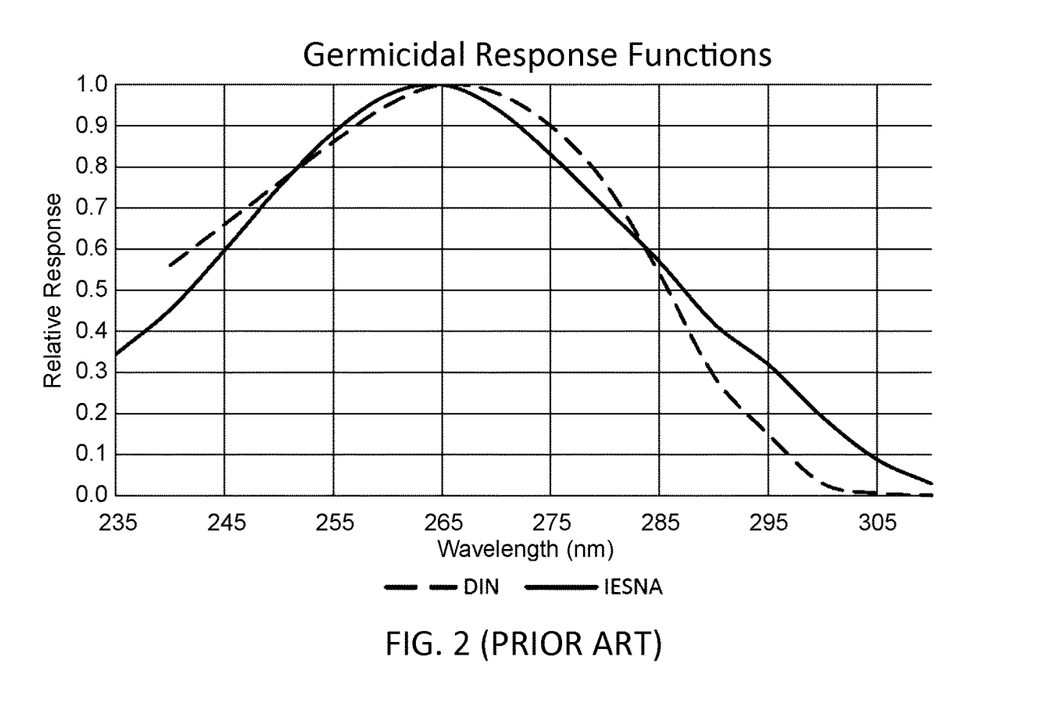
FIG. 2, prior art, shows the ultraviolet hazard function as a representation of the DNA spectral absorptance distribution from the German Institute for Standardization (DIN) and the Illuminating Engineering Society of North America (IESNA).

The susceptibility of bacteria and viruses to ultraviolet radiation varies by species and by the radiation wavelength. For bacteria and viruses containing DNA, the wavelength dependence is determined by the spectral absorbance of DNA. As shown in FIG. 2 (adapted from Table 2 of CIE 155:2003, Ultraviolet Air Disinfection), the range of effective wavelengths is approximately 200 nm to 310 nm, otherwise identified as within the range of ultraviolet-C (UV-C) radiation (100 nm to 280 nm) and ultraviolet-B (UV-B) radiation (280 nm to 315 nm). UV-B radiation is carcinogenic and relatively ineffective as a disinfection agent, and so UV-C radiation is most commonly employed for the purpose.

There are three common methods for determining the susceptibility of pathogens to UV-C radiation in the laboratory: 1) irradiation of pathogen colonies on a culture plate or Petri dish; 2) irradiation of pathogens suspended in water; and 3) irradiation of aerosolized particles. Once this has been determined for a pathogen species of interest, an ultraviolet germicidal irradiation (UVGI) system can be designed for an enclosed space, such as for example a hospital room or ward.

As can be seen from FIG. 2, the peak susceptibility of pathogens to UV-C occurs at about 270 nm. Low-pressure mercury-vapour lamps—basically linear fluorescent lamps with fused quartz rather than soda-lime glass tubes and without phosphor coatings—emit monochromatic UV-C radiation at 254 nm. At this wavelength, the susceptibility is about 85% of that of the peak susceptibility at 270 nm, but the lamps are still effective germicidal agents.

A disadvantage of 254 nm radiation is that it poses a photobiological risk to occupants in the "lower room." Care must be taken to ensure that the exposure to UV-C irradiance over time (referred to as the UV-C "dose") does not exceed the Threshold Limit Values (TLVs) established by the American Conference of Governmental Industrial Hygienists. Excess exposure can result in photokeratitis ("snow blindness"), photoconjunctivitis ("pink eye"), and erythema ("sunburn").

As noted for example by Kowalski, W. 2009 Ultraviolet Germicidal Irradiation Handbook. Heidelberg, Germany: Springer in Section 9.6, Performance, "the effectiveness of upper room air disinfection depends on ultraviolet power, fixture location, local reflective surfaces, degree of air mixing between the stratum and lower room volume, microbial susceptibility, and relative humidity."

In relation to the above, Kowalski (2009) references Rudnick, S. N., and M. W. First. 2007. "Fundamental Factors Affecting Upper-Room Ultraviolet Germicidal Irradiation—Part II. Predicting Effectiveness," J. Occupational and Environmental Hygiene 4:352-362, wherein "ultraviolet power" is defined as the ultraviolet radiant flux (measured in watts) incident on a plane placed near an ultraviolet fixture (or "luminaire").

Rudnick and First (2007) further note that reflections of UV-C radiation from surfaces in the upper room can be important, and present an approximation based on Sumpner's Principle (e.g., Cuttle, C. 1991. "Sumpner's Principle: A Discussion," Lighting Research and Technology 23(2): 99-106). As will be obvious to one skilled in the art of illumination engineering, this is an extreme simplification that is appropriate for modeling empty rectangular rooms only (e.g., FIG. 1).

As will be further evident to one skilled in the art of illumination engineering, the design and analysis of UVGI systems is no different from that of architectural lighting design and analysis using visible light. If the radiant intensity distribution of the UV-C luminaire has been measured in an optical test laboratory and the UV-C reflectances of the room surfaces are known or can be estimated, the principles of architectural lighting design and analysis can be used to predict the distribution of UV-C radiation anywhere within an enclosed space.

The problem, however, is that architectural lighting design and analysis is concerned with the illuminance of physical and virtual surfaces. The design and analysis of UVGI systems, by comparison, is concerned with the "spherical irradiance" (also referred to as the "radiant fluence rate") at arbitrary positions within the volume of air in the upper room.

The CIE International Lighting Vocabulary defines spherical irradiance as:

$$E_{e,o} = \int_{4\pi} L_e d\Omega \qquad (1)$$

with $d\Omega$ being the solid angle of each elementary beam of radiation passing through the given point, and $L_e$ is its radiance at that point. It further defines "radiant fluence" $H_{e,o}$ as the time integral of the spherical irradiance $E_{e,o}$ at a given point over a given duration:

$$H_{e,o} = \int_{\Delta t} E_{e,o} dt \qquad (2)$$

Conceptually, radiant fluence (also referred to as "dose" in medical literature) is the quotient of the radiant energy of all radiation incident upon the outer surface of an infinitesimally small sphere centered at the given point by the area of the diametrical cross-section of the sphere. With typical diameters of 0.5 to 5.0 micrometers, aerosolized viruses and bacteria may be considered as elementary spheres for the purposes of optical radiation design and analysis.

Rudnick and First (2007) note that the radiant fluence rate: " . . . is difficult and time consuming to measure because the fluence rate in the irradiated zone can vary considerably in both vertical and horizontal directions. Therefore, a large number of measurements must be made, particularly near the fixture where the fluence rate changes considerably over relatively short distances. In addition, the measurement must include the UV energy arriving from all directions; thus, a flat detector should not be used close to a UV source or if the room contains multiple UV sources."

Figure 3:
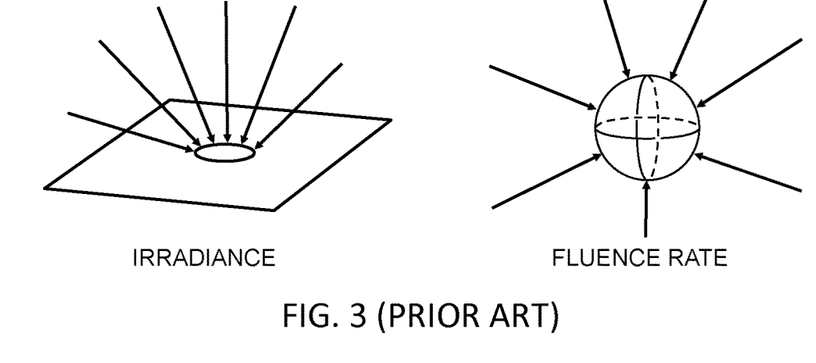
FIG. 3, prior art, illustrates the difference between the irradiance of a point on the surface of a plane and the spherical irradiance (fluence rate) of an elementary sphere.

The "flat" detector referred to by Rudnick and First (2007) is a conventional ultraviolet radiometer with a sensor that measures the irradiance of a plane, such as the Model 8.0-RP UVC meter with Remote Probe manufactured by Solarmeter (Glenside, Pa.). In terms of architectural lighting design and analysis, it is equivalent to an illuminance meter (FIG. 3).

Kowalski (2009) recommended in Section 9.7, Testing that, "When multiple fixtures exist in a room and face each other on opposite walls, the question may arise as to how to handle the measurements. It is appropriate in such cases to take two measurements facing opposite and add them directly, provided that there are no additional fixtures contributing to the local irradiance field. The result of this approach will approximate the same result obtained through the use of spherical sensors, such as are used in spherical actinometry." For ultraviolet measurements, these "spherical sensors" are typically comprised of centimeter-diameter quartz spheres that are filled with a chemical such as ferrioxalate, persulfate or iodide/iodate; their transmittance after exposure is linearly proportional to the UV-C fluence.

The measurement procedures recommended by Rudnick and First (2007) and Kowalski (2009) measure a rough approximation of the spherical irradiance when multiple luminaires are present, but they do not take reflection of ultraviolet radiation from room surfaces into consideration. More accurate measurements can be made using an AMOUR (Advanced Multi-purpose USB Radiometer) with a "scalar irradiance" (a synonym for spherical irradiance) collector and a narrowband ultraviolet filter as manufactured by Biospherical Instruments (San Diego, Calif.). However, such an instrument has a "blind spot" of approximately 80 degrees where the spherical Teflon™ collector is mounted on its connector shaft.

These measurement procedures are, however, relevant to testing and commissioning an as-built UVGI system only; they do not assist in the design and analysis of the system prior to construction.

The design and analysis procedures for empty rectangular rooms described for example in Kowalski (2009) are usually sufficient for hospital rooms and wards. However, recent research has determined that far-ultraviolet (far-UV) radiation (specifically 222 nm radiation emitted by krypton-chlorine excimer lamps) likely does not pose the photobiological risks of 254 nm radiation generated by low-pressure mercury-vapour lamps (e.g., Buonanno, M., et al. 2020. "Far-UVC Light (222 nm) Efficiently and Safely Inactivates Airborne Human Coronaviruses," Scientific Reports 10:10285). Referring to FIG. 2, and extrapolating, the germicidal efficacy of 222 nm radiation is 3.8 times less than that of 254 nm radiation. Nevertheless, it may be practical to directly irradiate the occupied lower room as well as the upper room. This opens up the possibility of disinfecting the air in public gathering spaces, including hotel and bank lobbies, restaurant dining areas and kitchens, airport lounges, movie theatres and playhouses, and more. These spaces may include both new building construction and building retrofits.

In order to maximize the efficacy of the far-UV disinfection, it is necessary to model the air flow through the gathering space. The reduction in viral load of the aerosols is determined by the total UV-C fluence over a given period of time. There must therefore be a balance between the fluence rate and the air flow rate to ensure that the air has been sufficiently disinfected.

Air flow modeling can be accomplished using computational fluid dynamics (CFD), typically based on the finite volume method. This requires being able to predict the radiant fluence rate within each small volume of the air flow model.

Given a complex architectural space with multiple ultraviolet luminaires whose radiant intensity distributions are known and a plurality of architectural surfaces whose reflectances within the spectral region of interest are known, there is therefore a need for a system and method of predicting the spherical irradiance at a multiplicity of points in free space within the virtual environment.

SUMMARY

For the purposes of this disclosure, there are three key parameters that influence pathogen reduction: 1) ultraviolet power; 2) fixture location; and 3) local reflective surfaces. Spherical irradiance is predicted in a model of an interior environment, which is to be disinfected, using spherical irradiance meters in a volume of interest in the environment. The spherical irradiance is provided by ultraviolet luminaires in the environment, and ultraviolet reflections from surfaces in the environment. A three-dimensional spherical irradiance field in the volume is interpolated from the spherical irradiances, and together with airflow calculations, is used to calculate radiant fluences in elemental volumes within the volume of interest. From the fluence, and a fluence response value of a pathogen, a predicted reduction in the pathogen in the interior environment is predicted. Irradiance sensors may be used in the ultraviolet luminaires for periodic reevaluation of the spherical irradiance field.

Disclosed is a method for predicting spherical irradiance for disinfecting an interior environment, the method comprising the steps of: positioning, by a processor, spherical irradiance meters in a model of the interior environment; calculating, by the processor, for each spherical irradiance meter, a total spherical irradiance; interpolating, by the processor, the total spherical irradiances to result in a three-dimensional spherical irradiance field; and calculating, by the processor, using the three-dimensional spherical irradiance field and a fluence response value of a pathogen, a predicted reduction in the pathogen in the interior environment.

Also disclosed is a system for predicting spherical irradiance for disinfecting an interior environment, the system comprising a processor and a non-transient computer-readable memory storing instructions, which, when executed by the processor, cause the processor to: position spherical irradiance meters in a model of the interior environment; calculate, for each spherical irradiance meter, a total spherical irradiance; interpolate the total spherical irradiances to result in a three-dimensional spherical irradiance field; and calculate, using the three-dimensional spherical irradiance field and a fluence response value of a pathogen, a predicted reduction in the pathogen in the interior environment.

DETAILED DESCRIPTION

Figure 4:
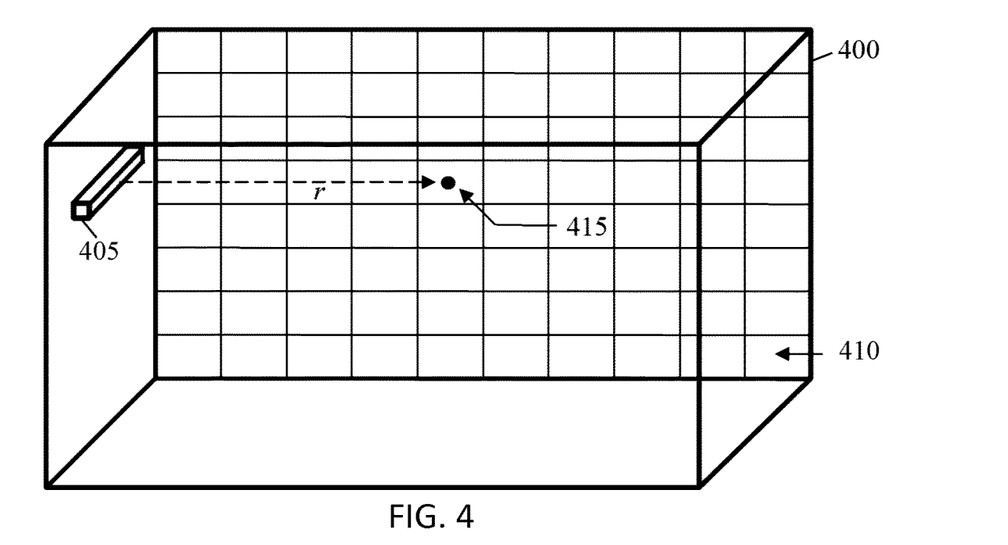
FIG. 4 shows an empty rectangular room with one example surface subdivided into patches.

Referring to FIG. 4, an empty rectangular room 400 has its surfaces subdivided into an array of patches 410 that are irradiated by an ultraviolet luminaire 405. Known radiosity methods as described in, for example, Ashdown, I. 1994. Radiosity: A Programmer's Perspective. New York, N.Y.: Wiley, may be employed to calculate the radiant exitance M of each patch 410 due to direct irradiance $E_o$ from one or more luminaires 405 and indirect irradiance $E_i$ received from all other patches visible to the patch and multiplied by the patch diffuse reflectance ρ.

A virtual spherical irradiance meter 415 is positioned at an arbitrary point P in the space. If the meter is at a distance r that is approximately two or more times the diagonal width of the emission area of luminaire 405, the luminaire can be represented as a point source of irradiation at the center of the emission area, and the direct irradiance $E_o$ of the spherical irradiance meter calculated using the inverse square law:

$$E_o = I_P/r^2 \qquad (3)$$

where $I_P$ is the radiant intensity of the luminaire in the direction of the point P.

If the distance r is less than the twice the diagonal width of the emission area of luminaire 405, the emission area may be subdivided into a one- or two-dimensional array of smaller subareas such that the diagonal width of each subarea satisfies the distance criterion, and the total radiant flux Φ emitted by the luminaire is evenly divided between them.

The inverse square law calculation is repeated for each luminaire 405 that is directly visible from the point P, to determine the total direct spherical irradiance $E_o$ at point P.

Figure 5:
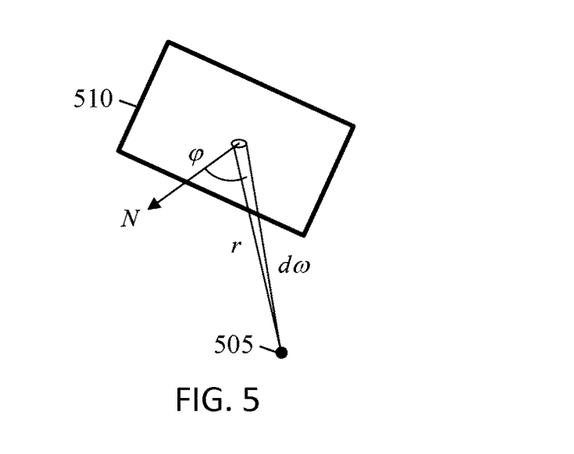
FIG. 5 shows the spherical irradiance received at a point from a single patch.

To calculate the indirect spherical irradiance $E_i$ from each patch 410 visible to point P, and referring to FIG. 5, it is first noted that the radiant flux E received at point 505 from a patch 510 with surface area A and radiant exitance $M_e$ that is at a distance r and at an angle φ to the surface normal N is:

$$E = \frac{1}{\pi} \int_\Omega M_e d\omega \qquad (4)$$

where the differential solid angle dω is defined as:

$$d\omega = \cos(\varphi) dA/r^2 \qquad (5)$$

Figure 6:
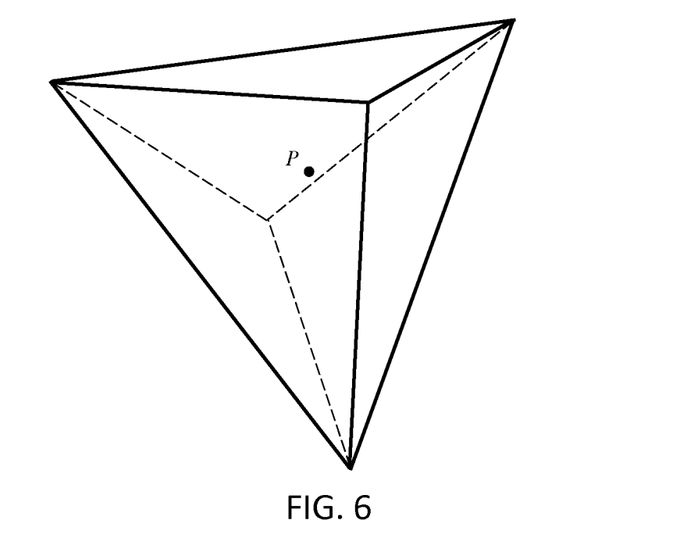
FIG. 6 shows a dual cubic tetrahedron as a component of a light buffer.
Figure 7:
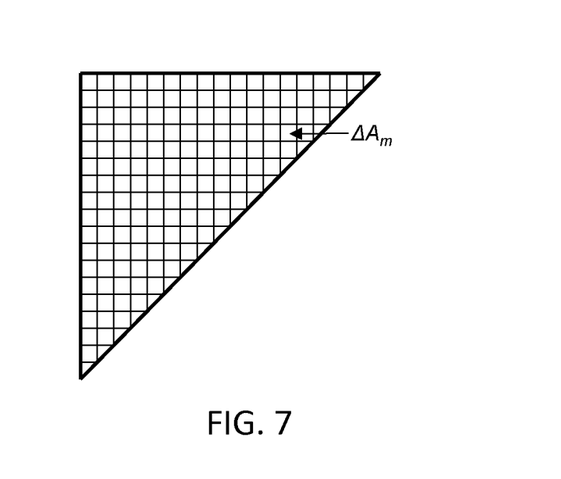
FIG. 7 shows the subdivision of a cubic tetrahedron face into an array of elements.

The integration can be performed by numerical quadrature using a "light buffer." This consists of two back-to-back cubic tetrahedrons measuring two units on each side that are centered on the point P (FIG. 6). Each face of the cubic tetrahedrons is divided into an array of n=m×m/2 cells with area $\Delta A_m$, as shown in FIG. 7. (The cells along the adjoining edges of the two tetrahedrons have area $\Delta A_m/2$.) Thus, for a given patch j, and a given face of the convex polyhedron from which the patch j is visible:

$$E_i \approx \frac{1}{\pi} \sum_n M_e \cos(\varphi_j) \Delta A_m / r_j^2 \qquad (6)$$

Figure 8:
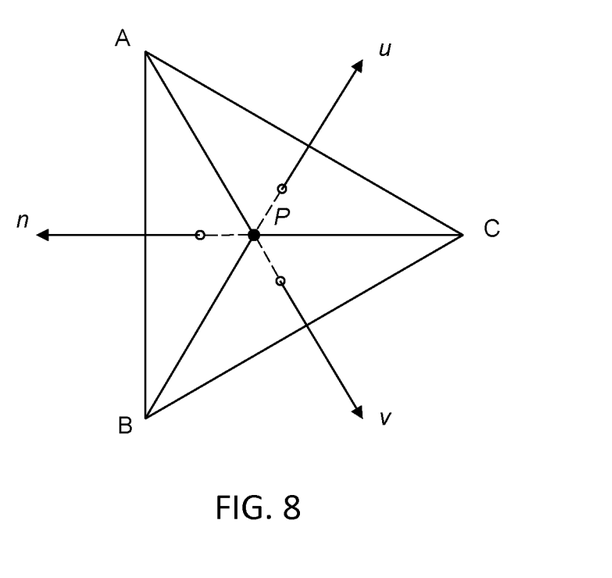
FIG. 8 shows the orientation of a light buffer with respect to the u-v-n Cartesian coordinate system.

FIG. 8 shows an orthographic projection of the upper cubic tetrahedron of a light buffer aligned on a horizontal plane with a u-v-n Cartesian coordinate system centered on point P and oriented such that each axis intersects a face of the cubic tetrahedron at a distance of unity from point P.

Taking the cubic tetrahedron face intersected by the n-axis as an example, we have for each cell with variable coordinates $u_n$ and $v_n$:

$$r_n = \sqrt{u_n^2 + v_n^2 + 1} \qquad (7)$$

and:

$$\cos(\varphi_n) = 1/r_n \qquad (8)$$

Thus, for a given patch, its contribution of indirect spherical irradiance to a given cell in a face of the cubic tetrahedron from which the patch is visible is:

$$\Delta E_i = M_e \Delta A_m / \pi (u_n^2 + v_n^2 + 1)^{3/2} \qquad (9)$$

and similarly for all six faces of the light buffer.

This can be confirmed by assuming a uniform sphere with unit radiant exitance surrounding the light buffer and centered on point P. A diffusely-emitting surface with radiant exitance M has radiance M/π in any direction, which gives:

$$\Delta E_i = \Delta A_m / (u_n^2 + v_n^2 + 1)^{3/2} \qquad (10)$$

Summing $\Delta E_i$ over all n cells (in the limit $\Delta A_n \to 0$) for each side yields 4π, which is the area of a unit sphere.

Referring to FIG. 8, the cubic tetrahedron faces are oriented with respect to the u-v-n Cartesian coordinate system such that:

$$A = \{-\sqrt{1/6}, \sqrt{1/2}, 0\}$$

$$B = \{-\sqrt{1/6}, -\sqrt{1/2}, 0\}$$

$$C = \{\sqrt{2/3}, 0, 0\}$$

$$D = \{0, 0, 0\}$$

$$u_{CT} = \{\sqrt{1/6}, \sqrt{1/2}, \pm\sqrt{1/3}\}$$

$$v_{CT} = \{\sqrt{1/6}, -\sqrt{1/2}, \pm\sqrt{1/3}\}$$

$$n_{CT} = \{-\sqrt{2/3}, 0, \pm\sqrt{1/3}\}$$

$$apex = \{0, 0, \pm\sqrt{1/3}\}$$

where the ± symbols are positive for the upper cubic tetrahedron, and negative for the lower one.

Figure 9:
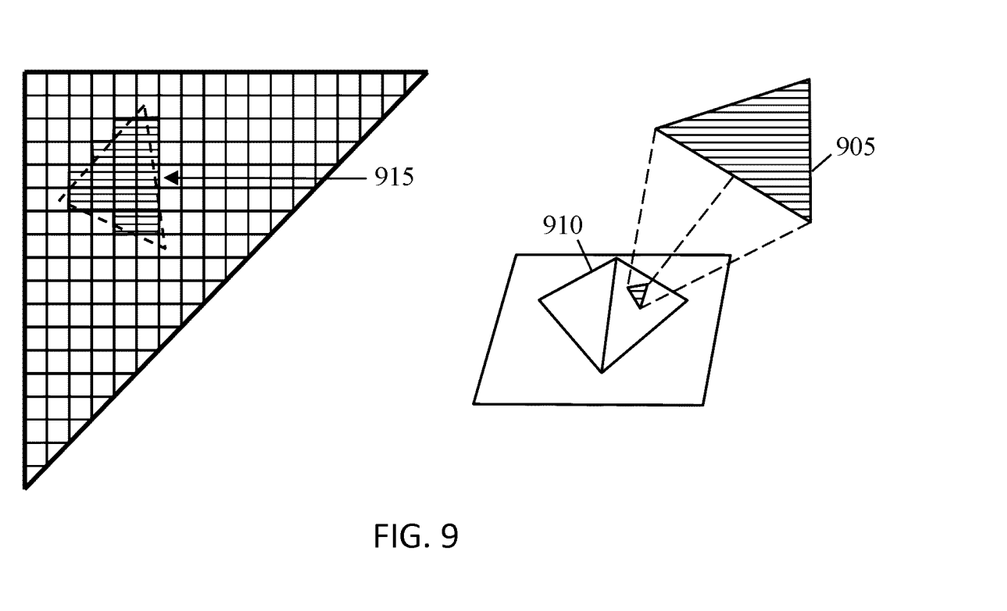
FIG. 9 shows a patch being projected onto the face of a cubic tetrahedron.

FIG. 9 shows a triangular patch 905 being projected onto a face of a cubic tetrahedron 910, where the projection covers the set of face cells 915, wherein the projection process is disclosed in for example Chapter 5 of Ashdown, I. 1994. Radiosity: A Programmer's Perspective. New York, N.Y.: Wiley.

Referring to FIG. 5, the differential solid angle dω is mathematically and conceptually equivalent to a ray that extends from the point 505 to a point on the surface of patch 510. Assuming that the patch p has constant radiant exitance $M_p$ and emits, transmits or reflects radiant flux in an ideal diffuse manner, the radiance $L_p$ of the patch will be $M_p/\pi$. Further, the luminance of the ray anywhere along its length will also be $L_p$. From this, it is evident that Equation 1 can be solved by summing the radiance of all rays with origins at point 505.

More practically, an approximate solution to Equation 1 is:

$$E_{e,o} \approx \frac{1}{\pi} \sum_n M_p \Delta\Omega \quad (11)$$

where n is the number of rays "cast" from point 505 into the environment in regular or random directions and $M_p$ is the radiant exitance of the patch intersected by the ray. Assuming a sufficient number of rays, $\Delta\Omega$ is equal to the area of a unit sphere ($4\pi$) divided by n.

A more accurate determination of the finite area $\Delta\Omega$ can be determined by performing a Voronoi tessellation of the unit sphere using the ray-sphere intersections as seeds and calculating the area of each Voronoi cell. The Voronoi tessellation may be determined using for example the algorithm disclosed in Na, H.-S., C.-N. Lee, and O. Cheong. 2001. "Voronoi Diagrams on the Sphere," Computational Geometry: Theory and Applications 23(2):183-194.

Figure 10:
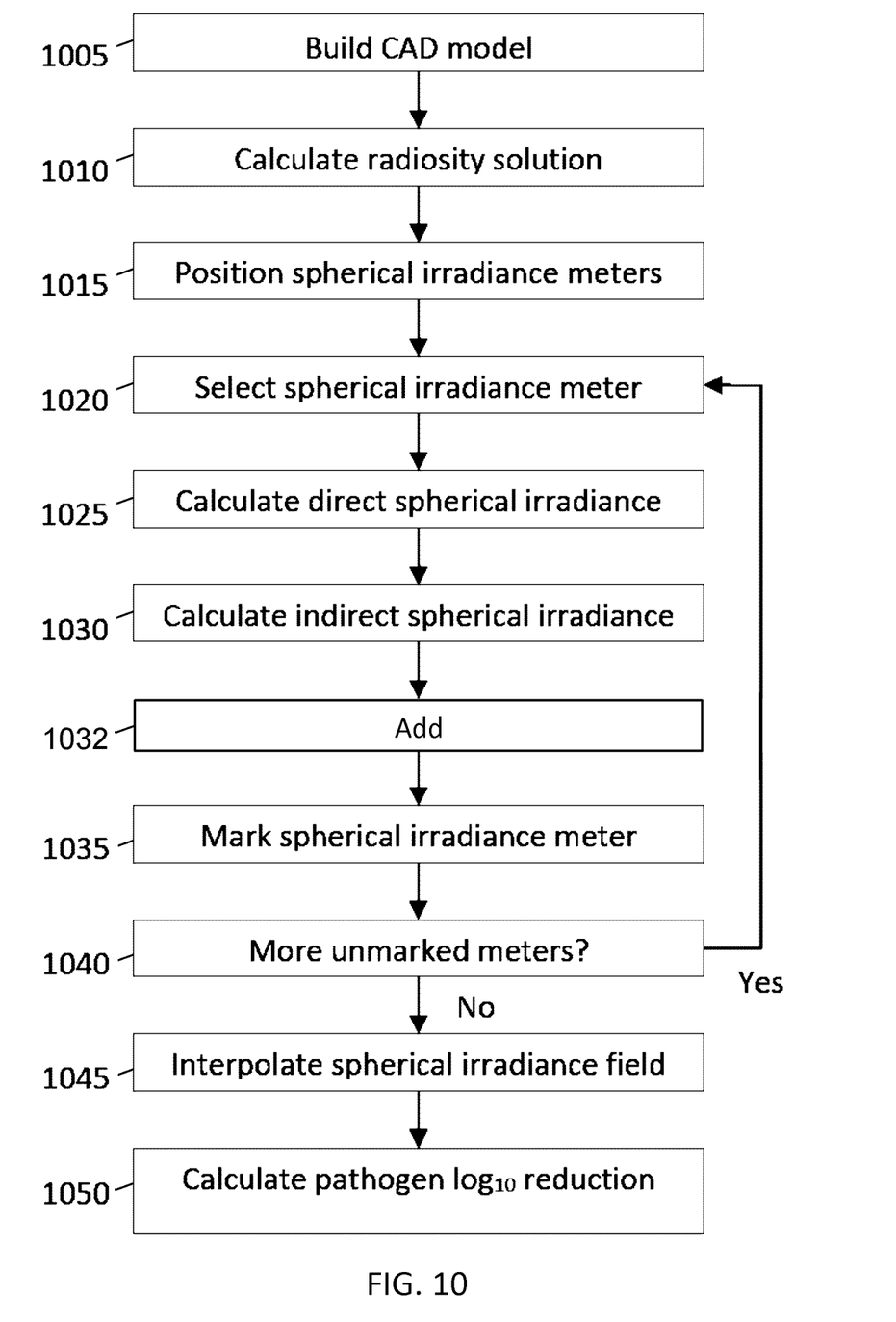
FIG. 10 shows a flowchart of a method of predicting a three-dimensional spherical irradiance field in a virtual environment, according to an embodiment of the present invention.

A method of predicting the three-dimensional spherical irradiance field in an interior environment such as a complex architectural space is shown in FIG. 10. In step 1005, a three-dimensional computer-aided drafting (CAD) model of the interior environment is prepared, including ultraviolet reflectance values for each material and radiant intensity distributions for each ultraviolet luminaire positioned within the interior environment. The model exists as a virtual environment that represents the interior environment.

In step 1010, a radiosity solution for the virtual environment is calculated, as described in detail in Ashdown (1994). This will produce an ultraviolet radiant exitance value for each patch of the meshed surfaces of the model. (As will be understood by one skilled in the art, other global illumination techniques such as photon mapping may also be used to determine the spatial distribution of radiant exitance over the set of surface patches.)

In step 1015, a three-dimensional array of spherical irradiance meters is positioned within the virtual environment, with at least one within each volume of interest for air flow calculations using CFD techniques. The array may be regular or partially random for example, or the spherical irradiance meters may be positioned randomly. The volumes of interest may be, for example, those making up an upper area of a room, i.e. above about 2.1-2.5 m. In other cases, the volumes of interest may cover a portion of an upper area of a room. In yet other cases the volumes of interest may include the whole of the space in the interior environment.

In step 1020, a spherical irradiance meter is selected from the set of one or more arrays.

In step 1025, the direct spherical irradiance due to all of the ultraviolet luminaires either fully or partially visible to the spherical irradiance meter is calculated in accordance with the inverse square law (Equation 3). The result is a total direct spherical irradiance for the selected irradiance meter.

In step 1030, the indirect spherical irradiance due to all surface patches fully or partially visible to the spherical irradiance meter is calculated using numerical integration with a light buffer as disclosed herein (Equation 9) and described in further detail in Ashdown (1994). Alternatively, the indirect spherical irradiance can be calculated using the ray casting technique (Equation 11). The result is a total indirect spherical irradiance for the selected irradiance meter.

In step 1032, the total direct spherical irradiance and total indirect spherical irradiance for the selected irradiance meter are added together to result in a total spherical irradiance for the selected irradiance meter.

In step 1035, the spherical irradiance meter is marked as having been processed.

In step 1040, the set of spherical irradiance meters is searched for unmarked meters. If one is found, control returns to step 1020; otherwise control proceeds to step 1045. In other embodiments, there may be other ways of selecting the next spherical irradiance meter, for example they may be numbered.

In step 1045, the three-dimensional spherical irradiance field is trilinearly or tricubically interpolated from the virtual spherical irradiance meter measurements in accordance with the spatial resolution requirements of a CFD program. In other embodiments, other methods of interpolation may be used, where interpolation includes any way of estimating new data points between or within a discrete set of known data points.

In step 1050, the CFD program is used to calculate the total radiant fluence (that is, the sum of spherical irradiances multiplied by time step) for each finite volume of air in the volume of interest. The CFD calculation divides the volume of interest into small, elemental volumes in order to perform its calculation. The total radiant fluence is used to calculate the $\log_{10}$ reduction in the pathogen species of interest within each of the finite volumes of air. The $\log_{10}$ reductions may then be combined for all volumes of interest in the virtual environment to result in a global $\log_{10}$ reduction for the virtual environment. Different pathogens have different susceptibilities to the total radiant fluence (i.e. fluence response values), and so the $\log_{10}$ reduction will be dependent on both the total radiant fluence and the type of pathogen.

In another embodiment, a different spectral range of optical radiation may be employed, including broadband ultraviolet radiation from pulsed xenon lamps (e.g., Nerandzic, M. M., et al. 2015. "Evaluation of a Pulsed Xenon Ultraviolet Disinfection System for Reduction of Healthcare-Associated Pathogens in Hospital Rooms," Infection Control & Hospital Epidemiology 36(2):192-197), visible light (e.g., Gillespie, J. B., et al. 2017. "Efficacy of Pulsed 405-nm Light-Emitting Diodes for Antimicrobial Photodynamic Inactivation: Effects of Intensity, Frequency, and Duty Cycle," Photomedicine and Laser Surgery 35(3): 150-156), and infrared radiation from infrared heaters.

In yet another embodiment, the medium may be a substantially transparent and optically non-diffusing fluid such as water, wherein ultraviolet light is employed for example to disinfect flowing water (e.g., Bolton, J. R., and C. A. Cotton. 2008. Ultraviolet Disinfection Handbook. Denver, Colo.: American Water Works Association), Water absorbs UV-C radiation, and so the Beer-Lambert law relating the attenuation of optical radiation to the distance it travels through an absorbing medium must be included in the calculation of both direct and indirect spherical irradiance. The distance from the spherical irradiance meter to each visible luminaire and each surface patch is known, and so this is easily incorporated into the calculations. For example, the inverse square law for direct spherical irradiance (Equation 3) become:

$$E_o = I_p e^{-\mu r}/r^2 \quad (12)$$

where $\mu$ is the absorption coefficient of the fluid for the specified wavelength range. (This coefficient is close to zero for pure distilled water, but is typically 0.01 to 0.2 cm$^{-1}$ for municipal drinking water due to dissolved iron, nitrate, manganese and organic matter.)

Similarly, for indirect spherical irradiance, Equation 9 becomes:

$$\Delta E_f \approx M_e \Delta A_m e^{-\mu d}/\pi(u_n^2 + V_n^2 + 1)^{3/2} \quad (13)$$

where d is the distance from the spherical irradiance meter to the nearest patch in the direction of the cubic tetrahedron face cell. (The distance d is available from the patch projection technique described in Ashdown 1994.)

Figure 11:
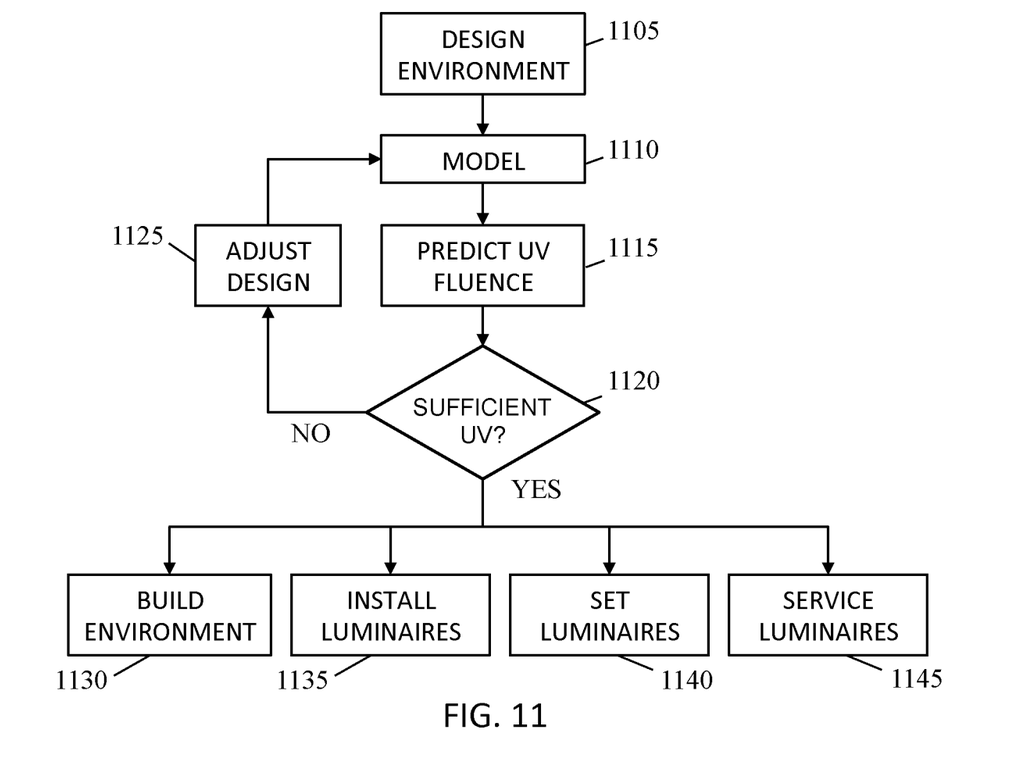
FIG. 11 is a flowchart for various implementations of the method, according to an embodiment of the present invention.

Referring to FIG. 11, a flowchart is shown of various applications of the method for predicting spherical irradiance. In step 1105, the interior environment is designed, and then modeled in step 1110 using a CAD program. In step 1115, the UV fluence is predicted, according to the method in FIG. 10, for example. In step 1120, a determination is made as to whether there will be sufficient UV fluence in the interior environment to cause the required reduction in pathogen density. If not, the design of the interior environment is adjusted in step 1125, for example by adding in more UV luminaires, by adjusting the placement of one or more of the UV luminaires, or by modifying the UV reflectivity of one or more of the surfaces in the interior environment. After adjusting the design, the interior environment model is rerun in step 1110. If there is sufficient UV fluence to kill the required amount of pathogens, then the process moves on. An action that may be taken may be, for example, building the environment, in step 1130, or modifying the construction of an existing environment. Other actions that may be taken may include the installation of UV luminaires, in step 1135, in an existing building, or upgrading existing UV luminaires in the building. In other cases, the UV luminaires may be adjusted to a different setting, or newly installed luminaires may be set, in step 1140. In step 1145, another possible action is to service one or more of the luminaires, since the output of them may have deteriorated over time, or dust may have accumulated on them, or on the reflective surfaces within the environment that contribute to the UV fluence. In one example, the model may be rerun in step 1110 later in time with downgraded luminaire specifications that take into account the expected deterioration in their performance, which may then result in the resetting of the luminaires in step 1140.

Figure 12:
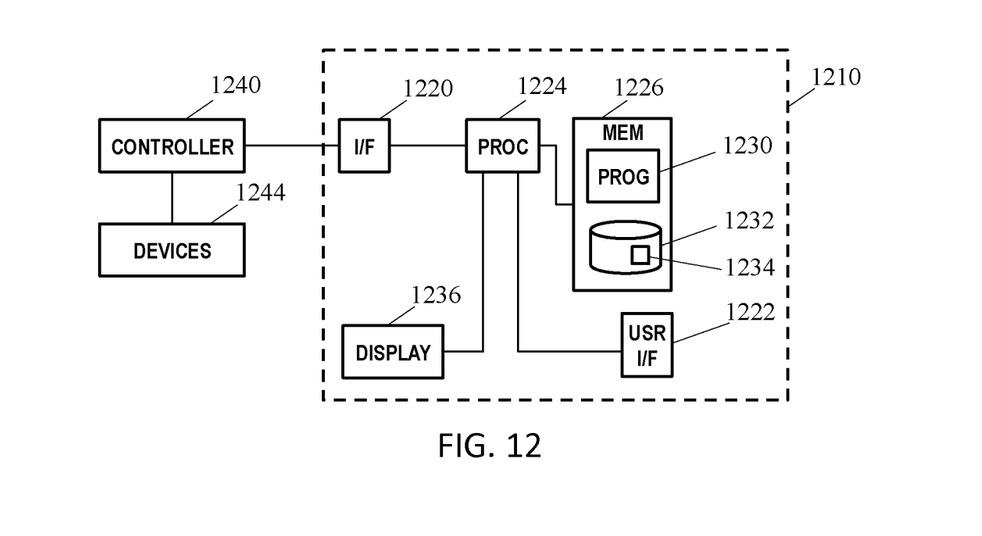
FIG. 12 is a schematic block diagram of a system for predicting UV spherical irradiance, according to an embodiment of the present invention.

Referring to FIG. 12, a system 1210 is shown for predicting UV spherical irradiance. A processor 1224, which may include multiple constituent processors, is connected to one or more interfaces 1220, 1222 and also to one or more computer-readable memories 1226 storing a program 1230 in the form of computer-readable instructions, which, when executed by the processor, cause the system to follow the processes described in relation to FIGS. 10 and 11. The memory 1226 also stores computer-readable data 1232, which is used by the processor 1224 to run the program 1230. The data 1232 is created by the program 1230, by an external program, or both. Data 1232 includes a model of a virtual environment 1234, which corresponds to the interior environment for which the spherical irradiance is being calculated. Data 1232 includes ultraviolet reflectance values for each material and radiant intensity distributions for each ultraviolet luminaire positioned within the interior environment. User interface 1222 and/or display 1236, allow a user to input or create a model of an environment for which the spherical irradiance is to be calculated, and to receive an output from the system that indicates the spherical irradiance is sufficient to meet desired targets of pathogen reduction, or that indicates the expected $\log_{10}$ reduction in pathogens in the interior environment. Interface 1220 may be connected to a controller 1240 for one or more luminaires and/or fenestration devices 1244 in the interior environment, which are controlled by the system to provide a desired level of UV fluence at a given time, and/or a desired lighting level for the occupants of the interior environment. The interface 1220 may be connected to the controller 1240 temporarily or permanently, or the connection between the controller and the interface 1220 may be for the transfer of data as and when needed, via one or more other computing devices or non-transient data storage devices.

The system 1210 includes a computer with sufficient calculation and graphics capability to prepare and display the virtual environment and calculate the total radiant fluence for each finite volume of air and the $\log_{10}$ reduction in the pathogen species of interest.

Figure 13:
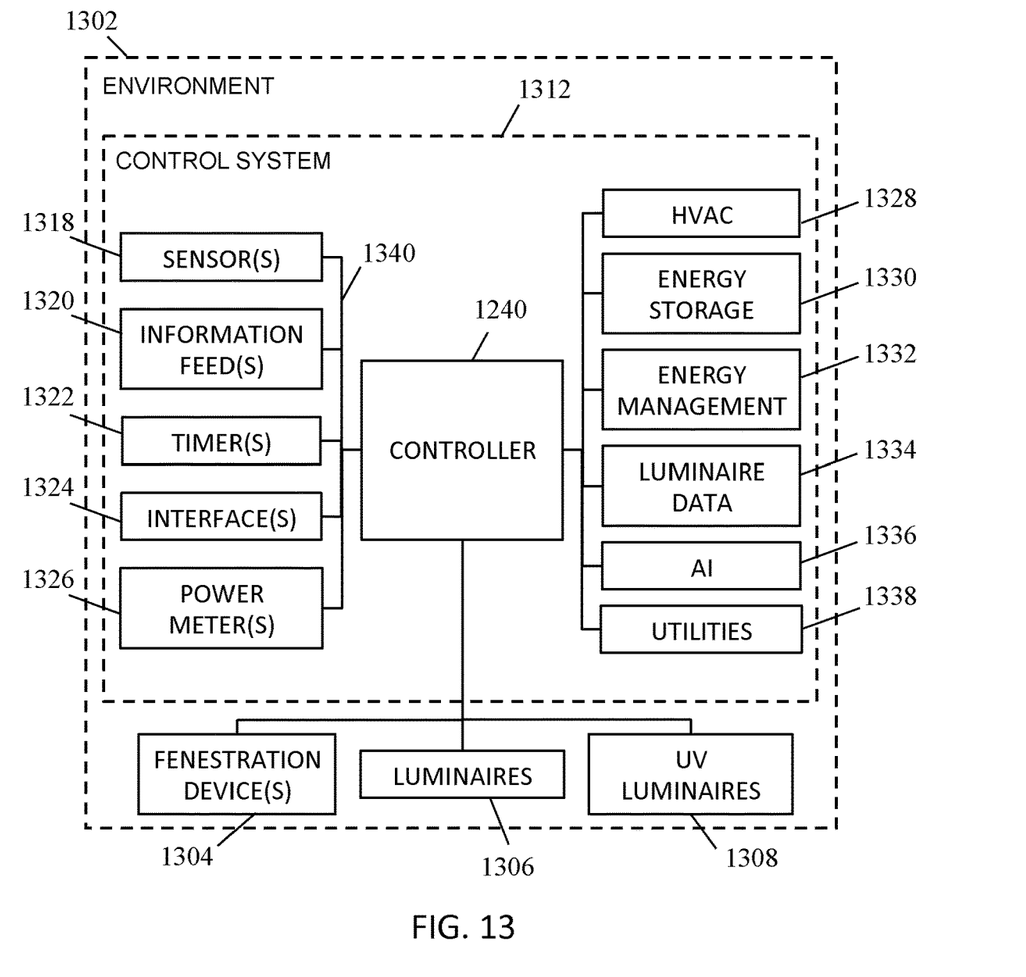
FIG. 13 is a schematic block diagram of a system for disinfecting an interior environment, according to an embodiment of the present invention.

Referring to FIG. 13, an interior environment 1302 is shown in which there are fenestration devices 1304, visible light luminaires 1306 and UV luminaires 1308. The controller 1240 may be part of a larger control system 1312 connected to multiple other components or systems.

The controller 1240 may read input data from a variety of sensors 1318 and information feeds 1320, the sensors and feeds including at least a plurality of sensors and information feeds from among the class of sensors and information feeds that includes UV photosensors, temperature sensors, occupancy sensors, humidity sensors, timers 1322, personal lighting controls (e.g. interfaces 1324), utility smart power meters 1326, HVAC 1328 and energy storage controllers 1330. The controller 1240 may also calculate the effects of variable building design parameters on building environment characteristics, such as upper air flow, and may output building design parameter setting command signals, in order to maximize energy savings while maintaining selected minimal occupant, including plant or animal, requirements for the building environment characteristics respectively. Minimum occupant requirements may include, for example, a temperature within a preset range, lighting within a preset range, pathogen density below a preset level, etc. The controller reads input data from a variety of sensors 1318 and information feeds 1320, including but not limited to UV photosensors, temperature sensors, occupancy sensors, humidity sensors, timers 1322, personal lighting controls 1324, utility power meters 1326, and other energy management systems 1332, including HVAC 1328 and energy storage controllers 1330. The controller 1240 receives and processes information 1334 about UV light fixtures 1308 and light sources (luminaires) 1306 located in a building's interior environment 1302, including photometric and electrical properties of the luminaires.

In one elementary form, the UVGI control system 1312 also includes: a) at least one controller 1240 that reads input data from a variety of sensors and information feeds, and includes an artificial intelligence engine 1336 or access to an artificial intelligence engine; b) at least one ambient condition sensor 1318 and at least one information feed 1320; and c) an interconnect system 1340 operatively coupling the controller to the sensor and the information feed, configured to provide output data suitable for dimming or switching ultraviolet luminaires 1308 and operating automated fenestration 1304 and other environmental devices.

The controller may further maintain communication with other building automation subsystems, including but not limited to HVAC 1328 and energy storage systems 1330. It may also maintain communication with external systems such as electrical power utilities 1338 and smart power grids.

In an exemplary mode of operation, the controller 1240 continually reads data from the external input and communication devices, calculates the optimal settings for the ultraviolet luminaires 1308, fenestration, and other environmental control devices, and controls those devices to achieve maximal annual energy savings while providing an interior luminous and thermal environment that is consistent with predefined goals and occupant preferences or plant or animal requirements. The "what-if" scenarios capability of the invention deriving from its simulating, using a virtual interior, a building interior environment on a regular basis (for example, hourly), enable a physical UVGI controller system to be designed and programmed accordingly. For example, the design may include an optimal layout of daylight photosensors. The controller may then further access the virtual representation of the interior environment during operation to refine its behavior in response to the building performance by means of "what-if" simulations.

Irradiation of aerosolized particles are possible with well-designed upper air UVGI systems incorporating UV-C, even as standalone controllers that function independently of the HVAC systems and other lighting systems. As such, the controller 1240 may control only UV luminaires in some embodiments.

Figure 14:
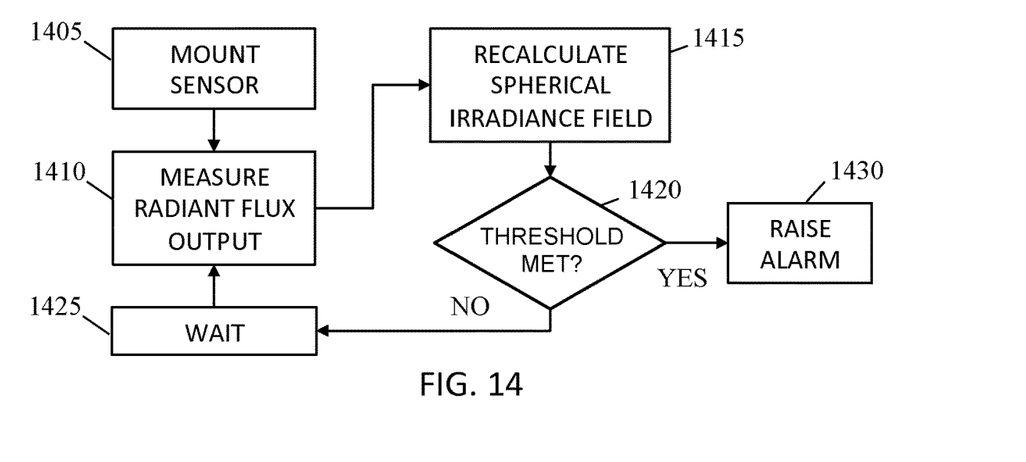
FIG. 14 is a flowchart of a method for ongoing monitoring of the spherical irradiance field, according to an embodiment of the present invention.

In a specific embodiment, referring to step 1405 of FIG. 14, a UV irradiance sensor is mounted within each radiation source in the interior environment in order to monitor its radiant flux output. In step 1410, the radiant flux output of each UV luminaire is measured. The measurement may be an absolute measurement or a relative measurement from which an absolute value may be determined. The radiant flux output will decrease over time due to radiation source degradation and dirt accumulation. Periodically, the relative radiant flux outputs of the radiation sources are measured, and the resulting values are used in the model of the interior environment to calculate the spherical irradiance field within the environment, in step 1415. In step 1420, the spherical irradiance field is compared to one or more threshold values of the spherical irradiance field. A threshold may be a minimum threshold that is necessary to provide at least a minimum amount of pathogen reduction in the interior environment. In other cases, a threshold may be a maximum threshold above which the amount of UV in the interior environment is dangerous to the occupants. If no thresholds are met, the process moves to step 1425, after which the radiant flux outputs are remeasured in step 1410. An alarm is issued in step 1430 when the spherical irradiance distribution does not satisfy the minimum and maximum design requirements, i.e. when the spherical irradiance field meets or exceeds a threshold. While the radiation sources may be monitored without using a model of the interior environment, there is no direct relationship between the performance of individual radiation sources and the resultant spherical irradiance distribution. As it is important to know the spherical irradiance distribution, or field, in order to predict the reduction in pathogens, use of the model of the interior environment is essential to calculate the spherical irradiance field. In other embodiments, the predicted reduction in pathogen is recalculated, and the comparison is made with a threshold level of pathogen reduction.

While the description has been given mainly in relation to UV spherical irradiance prediction, the invention also may be used for the prediction of infrared spherical irradiance.

Predicted reductions in pathogen levels are approximate, and desired values of such are to be understood to include tolerances that are normal in the field.

The embodiments of the invention may be varied in many ways. Such variations are not to be regarded as a departure from the scope of the invention, and all such modifications as would be obvious to one skilled in the art are intended to be included within the scope of the claims.

I claim:

1. A method for reducing pathogens in an interior environment, the method comprising the steps of:
   positioning, by a processor, spherical irradiance meters in a model of the interior environment;
   calculating, by the processor, for each spherical irradiance meter, a total spherical irradiance;
   interpolating, by the processor, the total spherical irradiances to result in a three-dimensional spherical irradiance field;
   calculating, by the processor, using the three-dimensional spherical irradiance field and a fluence response value of a pathogen, a predicted reduction in the pathogen in the interior environment; and
   controlling at least one ultraviolet luminaire in the interior environment to provide the predicted reduction.

2. The method of claim 1, comprising prior to the positioning step:
   preparing the model as a three-dimensional computer-aided drafting model; and
   calculating a radiosity solution for the interior environment.

3. The method of claim 1, wherein:
   the spherical irradiance meters are positioned in an array in a volume of interest for air flow calculations;
   the predicted reduction is calculated for the volume of interest;
   the interior environment comprises the at least one ultraviolet luminaire and zero or more further ultraviolet luminaires; and for each spherical irradiance meter, the total spherical irradiance is calculated by summing:
direct spherical irradiance on the spherical irradiance meter due to all of the ultraviolet luminaires that are either fully or partially visible to the spherical irradiance meter; and
indirect spherical irradiance on the spherical irradiance meter due to all surface patches of the model that are fully or partially visible to the spherical irradiance meter.

4. The method of claim 3, wherein calculating the predicted reduction comprises calculating, using the three-dimensional spherical irradiance field, a total radiant fluence for each of multiple finite volumes of air in the volume of interest.

5. The method of claim 1, wherein:
the interpolation step is performed trilinearly or tricubically; and
the predicted reduction is expressed as a $\log_{10}$ reduction.

6. The method of claim 1, comprising, after calculating each total spherical irradiance:
marking the spherical irradiance meter as having been processed; and
searching for a spherical irradiance meter that is unmarked.

7. The method of claim 1, wherein the total spherical irradiance is ultraviolet total spherical irradiance.

8. The method of claim 1, wherein the interior environment comprises air or water.

9. A method for predicting spherical irradiance for disinfecting an interior environment, the method comprising the steps of:
positioning, by a processor, spherical irradiance meters in a model of the interior environment;
calculating, by the processor, for each spherical irradiance meter, a total spherical irradiance;
interpolating, by the processor, the total spherical irradiances to result in a three-dimensional spherical irradiance field;
calculating, by the processor, using the three-dimensional spherical irradiance field and a fluence response value of a pathogen, a predicted reduction in the pathogen in the interior environment;
mounting an irradiation sensor in an ultraviolet luminaire in the interior environment;
periodically measuring, using the irradiation sensor, a radiant flux output of the ultraviolet luminaire;
using the radiant flux output and the model to recalculate the three-dimensional spherical irradiance field; and
comparing the recalculated three-dimensional spherical irradiance field or a recalculated predicted reduction in the pathogen to a threshold that results in an alarm being triggered if met.

10. A system for reducing pathogens in an interior environment, the system comprising:
a processor;
a non-transient computer-readable memory storing instructions, which, when executed by the processor, cause the processor to:
position spherical irradiance meters in a model of the interior environment;
calculate, for each spherical irradiance meter, a total spherical irradiance;
interpolate the total spherical irradiances to result in a three-dimensional spherical irradiance field; and
calculate, using the three-dimensional spherical irradiance field and a fluence response value of a pathogen, a predicted reduction in the pathogen in the interior environment; and
one or more ultraviolet luminaires that provide the predicted reduction in the interior environment.

11. The system of claim 10, comprising an irradiation sensor in one or more of the one or more ultraviolet luminaires, wherein the processor is configured to recalculate the total spherical irradiances using a measurement from each irradiation sensor.

12. A system for predicting spherical irradiance for disinfecting an interior environment, the system comprising:
a processor;
a non-transient computer-readable memory storing instructions, which, when executed by the processor, cause the processor to:
position spherical irradiance meters in a model of the interior environment;
calculate, for each spherical irradiance meter, a total spherical irradiance;
interpolate the total spherical irradiances to result in a three-dimensional spherical irradiance field; and
calculate, using the three-dimensional spherical irradiance field and a fluence response value of a pathogen, a predicted reduction in the pathogen in the interior environment; and
a controller which is connected to the processor and controls one or more ultraviolet luminaires in the interior environment to provide the predicted reduction.

13. The system of claim 12, connected to an occupancy sensor, an information feed, a timer, a user interface, a power meter, an HVAC (heating, ventilation and air conditioning) system, an energy storage system, an energy management system, an artificial intelligence engine, a utility company, a fenestration device or a visible luminaire, or any combination selected therefrom, and configured to provide minimum occupant requirements for occupants in the interior environment.

14. The method of claim 9, comprising prior to the positioning step:
preparing the model as a three-dimensional computer-aided drafting model; and
calculating a radiosity solution for the interior environment.

15. The method of claim 9, wherein:
the spherical irradiance meters are positioned in an array in a volume of interest for air flow calculations;
the predicted reduction is calculated for the volume of interest;
the interior environment comprises the ultraviolet luminaire and zero or more further ultraviolet luminaires; and
for each spherical irradiance meter, the total spherical irradiance is calculated by summing:
direct spherical irradiance on the spherical irradiance meter due to all of the ultraviolet luminaires that are either fully or partially visible to the spherical irradiance meter; and
indirect spherical irradiance on the spherical irradiance meter due to all surface patches of the model that are fully or partially visible to the spherical irradiance meter.

16. The method of claim 15, wherein calculating the predicted reduction comprises calculating, using the three-dimensional spherical irradiance field, a total radiant fluence for each of multiple finite volumes of air in the volume of interest.

17. The method of claim 9, wherein:
   the interpolation step is performed trilinearly or tricubically; and
   the predicted reduction is expressed as a $\log_{10}$ reduction.

18. The method of claim 9, comprising, after calculating each total spherical irradiance:
   marking the spherical irradiance meter as having been processed; and
   searching for a spherical irradiance meter that is unmarked.

19. The method of claim 9, wherein the total spherical irradiance is ultraviolet total spherical irradiance.

20. The method of claim 9, wherein the interior environment comprises air or water.

* * * * *